United States Patent
Leong Chung Wei

(10) Patent No.: US 8,478,009 B2
(45) Date of Patent: Jul. 2, 2013

(54) GENERATION AND ANALYSIS OF REPRESENTATIONS OF SKIN CONDITIONS

(75) Inventor: Bernard Leong Chung Wei, Singapore (SG)

(73) Assignee: Empire Technology Development, LLC, Wilmington, DE (US)

( * ) Notice: Subject to any disclaimer, the term of this patent is extended or adjusted under 35 U.S.C. 154(b) by 263 days.

(21) Appl. No.: 12/971,140

(22) Filed: Dec. 17, 2010

(65) Prior Publication Data

US 2012/0155722 A1 Jun. 21, 2012

(51) Int. Cl.
*G06K 9/00* (2006.01)
*G06K 9/62* (2006.01)
*G06K 9/70* (2006.01)
*G06K 9/68* (2006.01)
*G06K 9/74* (2006.01)

(52) U.S. Cl.
USPC ........... 382/128; 382/224; 382/225; 382/226; 382/227; 382/228

(58) Field of Classification Search
None
See application file for complete search history.

(56) References Cited

U.S. PATENT DOCUMENTS

| | | | |
|---|---|---|---|
| 7,826,878 B2 * | 11/2010 | Alfano et al. | 600/310 |
| 8,214,309 B1 * | 7/2012 | Khosla et al. | 706/14 |
| 2002/0067858 A1 * | 6/2002 | Lazaridis | 382/228 |
| 2002/0122596 A1 * | 9/2002 | Bradshaw | 382/226 |
| 2003/0026483 A1 * | 2/2003 | Perona et al. | 382/203 |
| 2003/0147558 A1 * | 8/2003 | Loui et al. | 382/225 |
| 2008/0101665 A1 * | 5/2008 | Collins et al. | 382/128 |
| 2008/0285862 A1 * | 11/2008 | Tu et al. | 382/228 |
| 2009/0144033 A1 * | 6/2009 | Liu et al. | 703/2 |
| 2009/0245603 A1 * | 10/2009 | Koruga et al. | 382/128 |
| 2009/0318815 A1 * | 12/2009 | Barnes et al. | 600/473 |
| 2010/0220906 A1 * | 9/2010 | Abramoff et al. | 382/130 |
| 2011/0301441 A1 * | 12/2011 | Bandic et al. | 600/306 |

OTHER PUBLICATIONS

Mies, C., Bauer, C., Ackermann, G., Baumler, W., Abels, C., Puntonet, C.G., Alvarez, M.R., and Lang, E.W., Can ICA Help Classify Skin Cancer and Benign Lesions?, 2001, Lecture Notes in Computer Science, vol. 2085/2001, pp. 328-335.*

Obrezanova, O., Csanyi, G., Gola, J.M.R., and Segall, M.D. Gaussian Processes: A Method for Automatic QSAR Modeling of ADME Properties, 2007, J. Chem. Inf. Model., vol. 47, pp. 1847-1857.*

(Continued)

*Primary Examiner* — Stephen R Koziol
*Assistant Examiner* — Jonathan S Lee
(74) *Attorney, Agent, or Firm* — Steven S. Rubin, Esq.; Moritt Hock & Hamroff LLP

(57) ABSTRACT

Technologies are generally described for methods and systems for generating a representation of a skin condition. The method may include receiving first image data relating to a first image of a skin condition and second image data relating to a second image of the skin condition. The method may further include performing a component analysis of the first and second image data to generate a first and second weighted component analysis results for the first and second image data. The weighted component analysis results may represent the respective image data as a weighted sum of components. The method may further include performing a sampling analysis to the weighted component analysis results to generate a weighted image representation for the skin condition. The weighted image representation may represent the skin condition as a weighted sum of the components.

20 Claims, 5 Drawing Sheets

OTHER PUBLICATIONS

Lin, C.T., Cheng, W.C., and Liang, S.F. An On-Line ICA-Mixture-Model-Based Self-Constructing Fuzzy Neural Network, 2005, IEEE Transactions on Circuits and Systems—I:Regular Papers, vol. 52, No. 1, pp. 207-221.*

Lappalainen, H. and Honkela, A., Bayesian Non-Linear Independent Component Analysis by Multi-Layer Perceptrons, 2000, Advances in Independent Component Analysis, pp. 93-121.*

Stockmeier, H.G., Baumler, W., Szeimies, R.M., Theis, F.J., Puntonet, C.G., and Lang, E.W., Classification of Skin Lesions by Fluorescence Diagnosis and Independent Component Analysis, 2004, Biomedical Engineering, pp. 1-4.*

Tabatabaie, K.; Esteki, A.; , "Independent Component Analysis as an Effective Tool for Automated Diagnosis of Melanoma," 2008, Biomedical Engineering Conference. CIBEC 2008. Cairo International, pp. 1-4.*

Adenle, O.A. and Fitzgerald, W.J., Bayesian Model Selection for Independent Factor Analysis, 2006, IEEE Information Theory Workshop, pp. 337-341.*

Tsumura, N., Ojima, N., Sato, K., Shiraishi, M., Shimizu, H., Nabeshima, H., Akazaki, S., Hori, K., and Miyake, Y., Image-based skin color and texture analysis/synthesis by extracting hemoglobin and melanin information in the skin, 2003, ACM Transactions on Graphics, vol. 22, No. 3pp. 770-779.*

Liu, X., Srivastava, A., Gallivan, K., Optimal Linear Representations of Images for Object Recognition, 2003, IEEE Computer Society Conference on Computer Vision and Pattern Recognition, vol. 1, pp. I-229-I-234.*

Hyvarinen, A., Oja, E., Independent component analysis: algorithms and applications, 2000, Neural Networks, vol. 13, pp. 411-430.*

Cheng, H.D., Shi, X.J., Min. R., Hu, L.M., Cai, X.P., and Du, H.N., Approaches for automated detection and classification of masses in mammograms, 2005, Pattern Recognition, vol. 39, pp. 646-668.*

Mukherjee, P., Parkinson, D., and Liddle, A.R., A nested sampling algorithm for cosmological model selection, 2008, The Astrophysical Journal Letters, vol. 638, No. 2, pp. 1-4.*

Peterson et al. (2000) "On the Independent Components of Functional Neuroimages"; Thor Center for Neuroinformatics, p. 1-6.

Liu et al. (2008) "Face Hallucination based on Independent Component Analysis"; IEEE, p. 3242-3245.

Moghaddam et al. (2000) "Bayesian Face Recognition"; Pattern Recognition, 33(11): p. 1771-1782.

Chen et al. (2008) "Integration of External Signaling Pathways with the Core Transcriptional Network in Embryonic Stem Cells"; Cell, 133: p. 1106-1117.

Loh et al. (2006) "The Oct4 and Nanog transcription network regulates pluripotency in mouse embryonic stem cells"; Nature Genetics, p. 1-10.

Down et al. (2005) "NestedMICA: sensitive inference of over-represented motifs in nucleic acid sequence"; Nucleic Acids Research, 33(5): p. 1445-1453.

Cardoso (1998) "Multidimensional Independent Component Analysis"; Proceedings of ICASSP; p. 1-4.

Bartlett et al. (2002) "Face Recognition by Independent Component Analysis"; IEEE Transactions on Neural Networks, 13(6): p. 1450-1464.

Nuzillard et al. (2000) "Blind Source Separation of Astronomical Images"; Proceedings of the Second International Workshop on Independent Component Analysis and Blind Signal Separation, p. 99-104.

Skilling (2006) "Nested Sampling for Bayesian Computations"; Proc. Valencia/ISBA 8th World Meeting on Bayesian Statistics Benidorm, p. 1-25.

"Nested Sampling Algorithm" retrieved from Wikipedia.org. on Sep. 14, 2010.

"Bayes Factor" retrieved from Wikipedia.org. on Sep. 14, 2010.

"Independent Component Analysis" retrieved from Wikipedia.org. on Sep. 14, 2010.

* cited by examiner

300 A computer program product.

302 A signal bearing medium.

304

At least one of:

One or more instructions for a method for method for generating a representation of a skin condition; or One or more instructions for storing, in a memory, image data, the image data including first image data relating to a first image of a skin condition and second image data relating to a second image of the skin condition; or One or more instructions for receiving, at a processor, the image data; or One or more instructions for performing, by the processor, a component analysis of the first image data to generate a first weighted component analysis result for the first image data, wherein the first weighted component analysis result represents the first image data as a weighted sum of components; or One or more instructions for performing, by the processor, the component analysis of the second image data to generate a second weighted component analysis result for the second image data, wherein the second weighted component analysis result represents the second image data as a weighted sum of the components; or One or more instructions for performing, by the processor, a sampling analysis to the first weighted component analysis result and the second weighted component analysis result to generate a weighted image representation for the skin condition, wherein the weighted image representation represents the skin condition as a weighted sum of the components.

| 306 A computer readable medium | 308 A recordable medium | 310 A communications medium |

Fig. 4

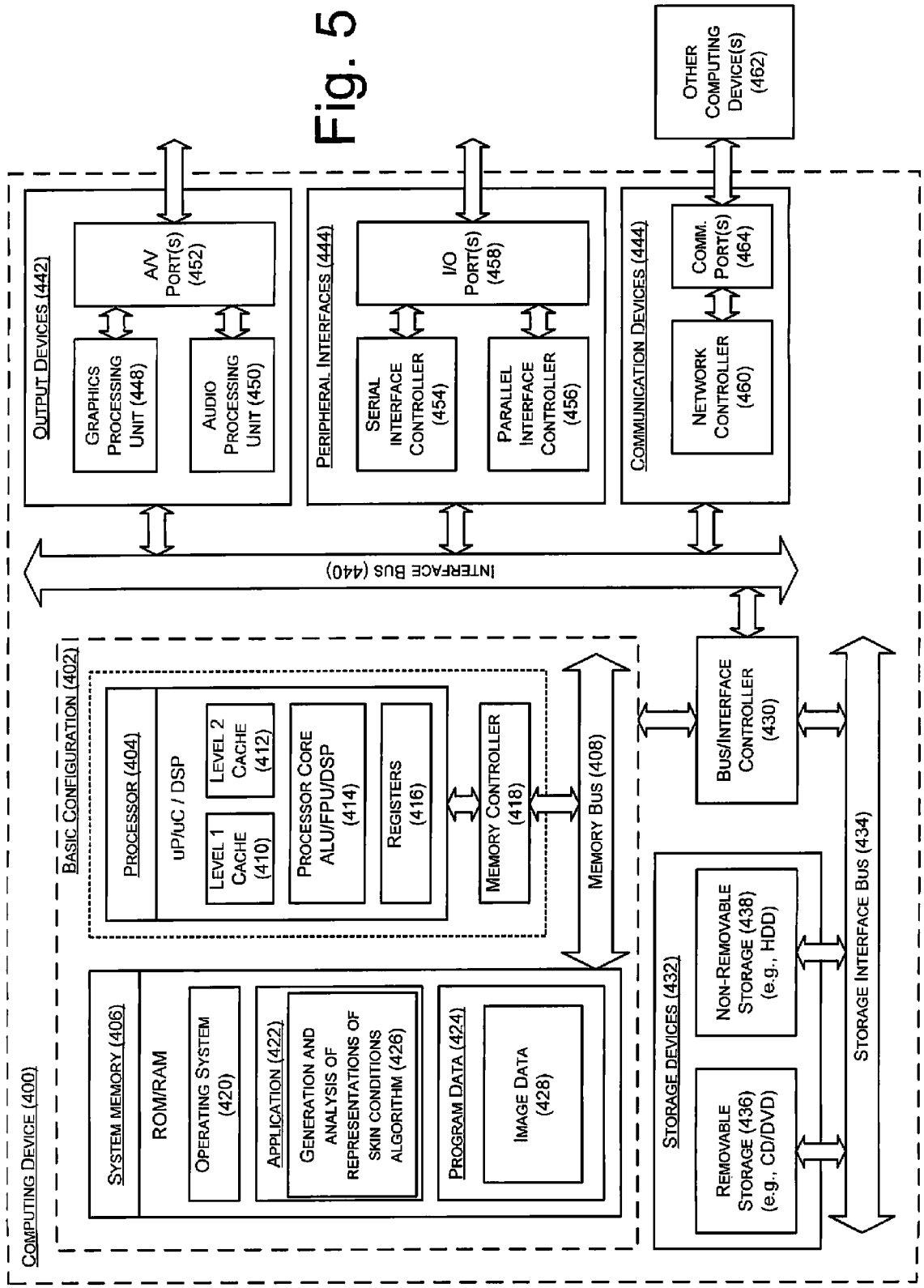

GENERATION AND ANALYSIS OF REPRESENTATIONS OF SKIN CONDITIONS

BACKGROUND

Unless otherwise indicated herein, the materials described in this section are not prior art to the claims in this application and are not admitted to be prior art by inclusion in this section.

Image recognition systems can identify representations of objects in images to be analyzed based on prior samples. The prior samples may be analyzed and analysis results may be stored. An image to be analyzed may be compared with the analysis results of prior samples to identify a representation of an object in the image to be analyzed.

SUMMARY

In an example, a method for generating a representation of a skin condition is generally described. In some examples, the method includes storing, in a memory, image data, the image data including first image data relating to a first image of a skin condition and second image data relating to a second image of the skin condition. The method may include receiving, at a processor, the image data. The method may include performing, by the processor, a component analysis of the first image data to generate a first weighted component analysis result for the first image data. The first weighted component analysis result may represent the first image data as a weighted sum of components. The method may include performing, by the processor, the component analysis of the second image data to generate a second weighted component analysis result for the second image data. The second weighted component analysis result may represent the second image data as a weighted sum of the components. The method may include performing, by the processor, a sampling analysis to the first weighted component analysis result and the second weighted component analysis result to generate a weighted image representation for the skin condition. The weighted image representation may represent the skin condition as a weighted sum of the components.

In an example, a system effective to generate a representation of a skin condition is generally described. The system may include a memory and a processor. In some examples, the memory may be configured to store image data. The image data may include first image data relating to a first image of a skin condition and second image data relating to a second image of the skin condition. The processor may be in communication with the memory. The processor may be effective to receive the image data and perform a component analysis of the first image data to generate a first weighted component analysis result for the first image data. The first weighted component analysis result may represent the first image data as a weighted sum of components. The processor may further be effective to perform the component analysis of the second image data to generate a second weighted component analysis result for the second image data. The second weighted component analysis result may represent the second image data as a weighted sum of the components. The processor may be effective to perform a sampling analysis to the first weighted component analysis result and the second weighted component analysis result to generate a weighted image representation for the skin condition. The weighted image representation may represent the skin condition as a weighted sum of the components. The processor may further be effective to store the weighted image representation in the memory.

In an example a method of analyzing image representations of skin conditions is generally described. The method may include storing, in a memory, image data of two or more images of two or more of skin conditions. The method may include receiving, at a processor, at least some of the image data of the two or more of images of the two or more of skin conditions. The method may include performing, by the processor, a component analysis of the at least some of the image data of the two or more of images of the two or more of skin conditions to generate a weighted component analysis result for the at least some of the image data. The method may further include performing, by the processor, a sampling analysis to two or more of weighted component analysis results of at least some of the two or more of skin conditions to generate a weighted image representation for the at least some of the two or more of skin conditions. The method may include storing, in the memory, the weighted image representation for the at least some of the two or more of skin conditions. The weighted image representation may include two or more weighted image components.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 4 illustrates example computer program products for implementing generation and analysis of representations of skin conditions; and FIG. 5 is a block diagram illustrating some example computing devices that are adapted to perform generation and analysis of representations of skin conditions; all arranged according to at least some embodiments presented herein.

DETAILED DESCRIPTION

Figure 1:
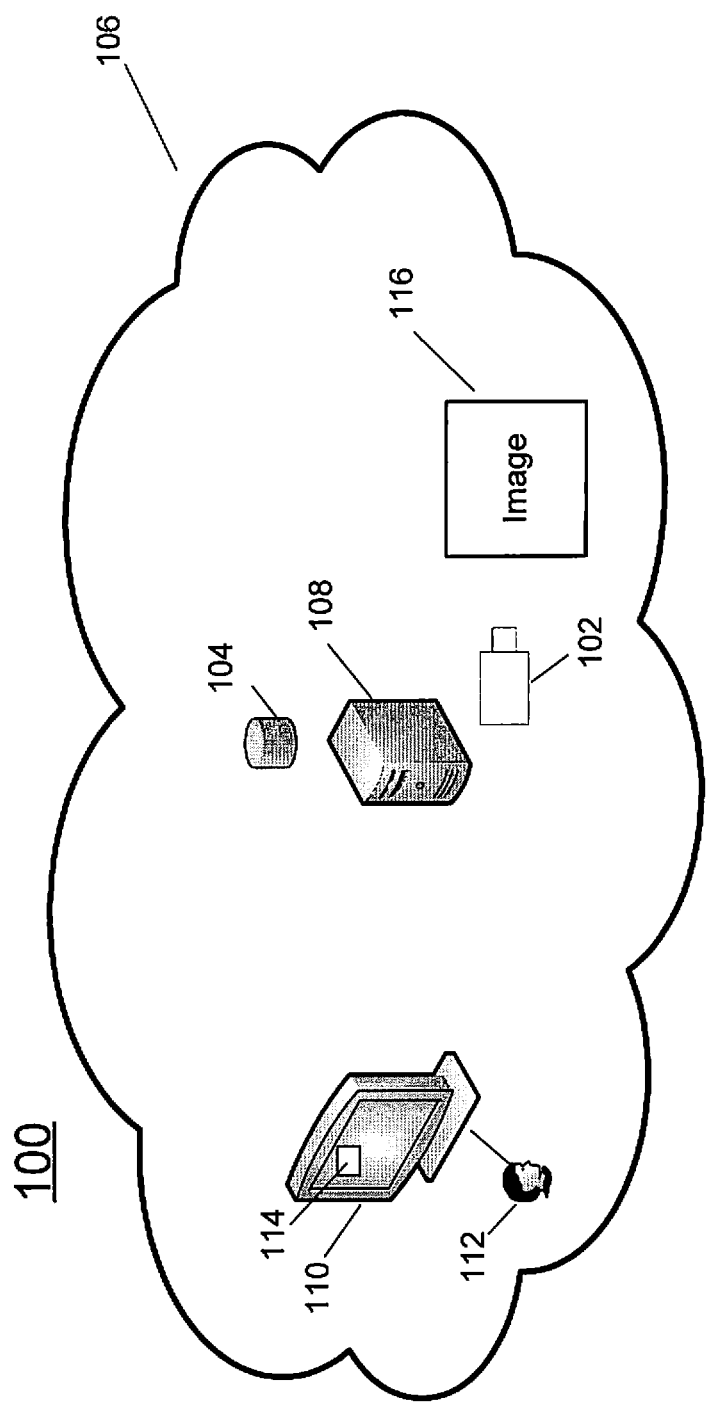
FIG. 1 illustrates some example systems that can be utilized to implement generation and analysis of representations of skin conditions.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the drawings, can be arranged, substituted, combined, separated, and designed in a wide variety of different configurations, all of which are explicitly contemplated herein.

This disclosure is generally drawn to, inter alia, methods, apparatus, systems, devices, and computer program products related to generation and analysis of representations of images and, in particular, of images of skin conditions.

Briefly stated, technologies are generally described for methods and systems for generating a representation of a skin condition. A method may include receiving first image data relating to a first image of a skin condition and second image data relating to a second image of the skin condition. The method may further include performing a component analysis of the first and second image data to generate a first and second weighted component analysis results for the first and second image data. The weighted component analysis results may represent the respective image data as a weighted sum of components. The method may further include performing a sampling analysis to the weighted component analysis results to generate a weighted image representation for the skin condition. The weighted image representation may represent the skin condition as a weighted sum of the components.

FIG. 1 illustrates some example systems that can be utilized to implement generation and analysis of representations of skin conditions arranged according to at least some embodiments presented herein. A system 100 may include a scanner 102, a memory 104 and a display 110 all arranged in communication with a processor 108. Processor 108 may be arranged in communication with scanner 102 and memory 104 through, for example, a network 106. Scanner 102 may be adapted to generate image data regarding at least one image 116. Scanner 102 may be further adapted to send the image data to processor 108. Processor 108 further may be adapted to retrieve a generation and/or analysis of representations of skin conditions algorithm(s) from memory 104. Using the generation and/or analysis algorithms, processor 108 may be adapted to generate a representation of and/or analyze a skin condition that may appear in image(s) 116. In some examples, the generation and/or analysis algorithms may include a component analysis and/or a sampling analysis as is explained in more detail below. Processor 108 may be adapted to display a generation and/or analysis result 114 on display 110 for viewing by a user 112 or store result 114 in memory 104.

Figure 2:
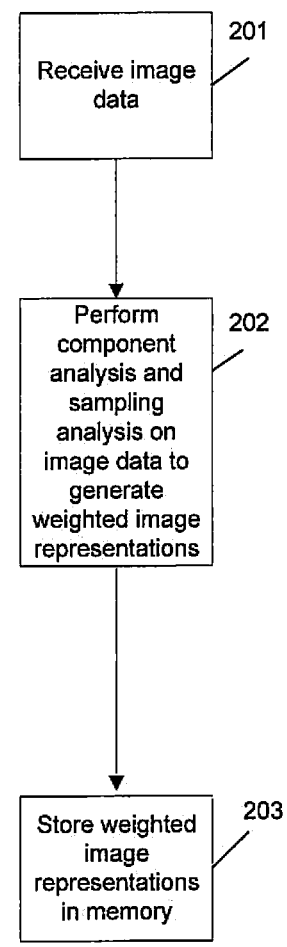
FIG. 2 depicts a flow diagram for example processes for implementing generation and analysis of representations of skin conditions.

FIG. 2 depicts a flow diagram for example processes for generation and analysis of representations of skin conditions arranged according to at least some embodiments presented herein. The process in FIG. 2 could be implemented using, for example, system 100 discussed above. An example process may include one or more operations, actions, or functions as illustrated by one or more of blocks 201, 202 and/or 203. Although illustrated as discrete blocks, various blocks may be divided into additional blocks, combined into fewer blocks, or eliminated, depending on the desired implementation. Processing may begin at block 201.

At block 201, a processor may be configured to receive first image data to be processed. In an example, the first image data can be received from a scanner or from a memory. The image data may relate to images to be analyzed, and, for example, may include images of skin conditions. The image data can include image data of multiple images of a first grouping of images, such as of a particular skin condition. The image data may also include image data of images of multiple groupings of images, such as of multiple skin conditions. Processing may continue from block 201 to block 202.

At block 202, the processor may be configured to perform a component analysis and a sampling analysis on the first image data to generate weighted image representations. The component analysis may utilize an independent component analysis (ICA) technique. In an ICA technique, the processor may be configured to receive a set of basis images or a set of components that, in a weighted combination, may represent other received images. The processor may be configured to represent an image or specific skin condition as a linear combination of the basis images or components. An image for a specific skin condition can be represented as a linear combination of basis images in the following form:

$$X_t = AS_t + V_t \qquad (1)$$

where $X_t$ is a vector representing an image observed at time t, A is a mixing matrix and $S_t$ is a source vector for the basis images. $V_t$ may be a noise vector that may be added if the data is too noisy or would benefit from noise cancellation processing. An ICA technique may be used to determine a combination of basis images or components given an observed image. Assuming a small noise vector, the image can be represented as:

$$X_t = AS_t \qquad (2)$$

The component analysis in block 202 may be based on basis images or components of an image such as color, contrast, tone, and/or gamma correction. For example, an image that is purple in color may be represented as a weighted combination of blue and red color components. The component analysis may process images on a component-by-component basis to express the image data as a weighted sum of components. The weighted component analysis result may represent the image data as the weighted sum of the components. The weighted component analysis result can be stored in a memory such as memory 104. The processor may be configured to perform a sampling analysis on the weighted component analysis results of images of each desired skin condition to generate respective weighted image representations for the skin conditions. Processing may continue from block 202 to block 203. At block 203, the processor may be configured to store the weighted image representations for the images of the skin conditions in a memory. For example, two or more weighted image representations for a skin condition may be stored.

In an example, the sampling analysis may generate a weighted image representation for the skin condition, based on the stored weighted image representations for the images of the skin condition. The weighted image representation for the skin condition may be a weighted sum of the components or basis images. For example, the sampling analysis may generate a single weighted image representation for a skin condition based on two or more stored weighted image representations of images of the skin condition. The sampling analysis may be utilized to determine the values for the mixing matrix A for the basis images S relating to a particular skin condition. In an example, a nested sampling analysis technique may be used. In some examples, in nested sampling analysis techniques, basis images or components may be sampled and sorted according to their likelihoods that they correspond to the skin condition. Nested sampling can represent values as contours on a likelihood distribution. For each cycle of the nested sampling, the least likely state may be discarded, and a new state may be sampled. Nested sampling allows multiple optimums of a probability landscape to be determined, which translates to the weights of the components for a specific skin condition.

In an example, at each cycle, nested sampling has N objects $A_1, \ldots, A_N$ with corresponding likelihoods $L(A_1), \ldots, L(A_N)$. The likelihood $L_i$ associated with each cycle i may be the lowest of the likelihood values, with j iterative steps. In an example, the sampling may stop after a threshold number of values have not changed between cycles. In an example, the following pseudo-code may be used:

```
//Start with N objects, A_1,..., A_N from prior iteration;
    initialize Z=0, D_0=1 and H=0;
//Repeat for i=1,2,..., j;
    record the lowest of current likelihood values as L_i;
    set D=exp(-i/N) or sample it to include its uncertainty;
    set w_i=D_{i-1}-D_i (simple) or D_{i-1}-D_{i+1}/2 (trapezoidal);
    increment Z by L_i w_i and update H, then
    replace object of lowest likelihood by new one drawn from within
        L(A) > L_i, in proportion to the prior iteration.
//Complete Z with N^{-1} (L(A_1) + ... + L(A_N))D_j
    where Z = one dimensional integral over unit range.
```

Figure 3:
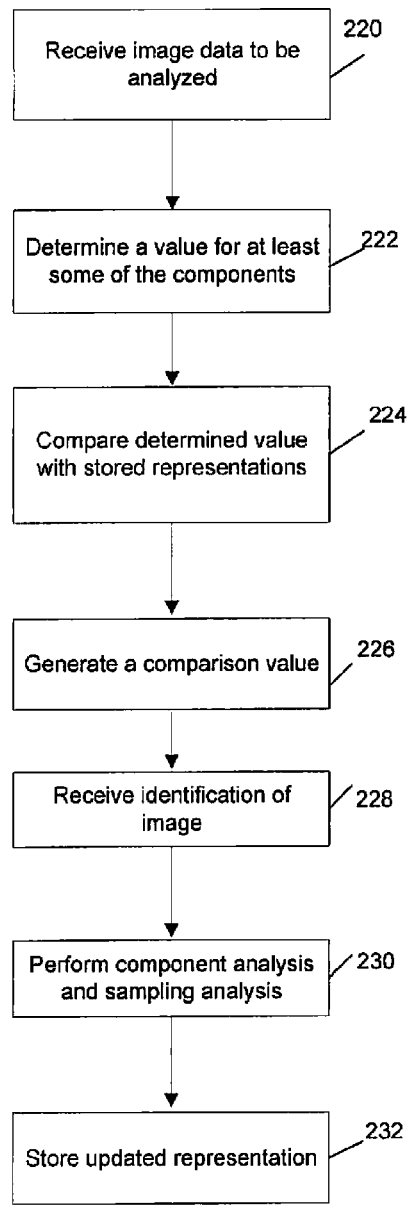
FIG. 3 depicts a flow diagram for example processes for implementing generation and analysis of representations of skin conditions.

FIG. 3 depicts a flow diagram for example processes for implementing generation and analysis of representations of skin conditions arranged according to at least some embodiments presented herein. The process in FIG. 3 could be implemented using, for example, system 100 discussed above. An example process may include one or more operations, actions, or functions as illustrated by one or more of blocks 220, 222, 224, 226, 228, 230 and/or 232. Although illustrated as discrete blocks, various blocks may be divided into additional blocks, combined into fewer blocks, or eliminated, depending on the desired implementation. Processing may begin at block 220.

At block 220, a processor may be configured to receive image data of an image to be analyzed. Processing may continue from block 220 to block 222.

At block 222, the processor may be configured to determine a value of at least some of image components of the image data of the image to be analyzed. In some examples, the image components relate to the components used in representing skin conditions as discussed above with reference to FIG. 2. Processing may continue from block 222 to block 224.

At block 224, the processor may be configured to compare the value of at least some of the image components of the image data of the image to be analyzed with a corresponding image component of a weighted image representation for one or more skin conditions. For example, a value of the color of the image to be analyzed may be compared with values of color components of stored weight image representations of one or more skin conditions. Processing may continue from block 224 to block 226.

At block 226, the processor may be configured to generate a comparison value based on the comparison. In some examples, the comparison value may represent a likelihood that the image to be analyzed corresponds to one or more of the skin conditions whose weighted image representation is stored. Processing may continue from block 226 to block 228.

In some examples, image data of an image X to be analyzed can be represented by Equation (3):

$$X=W_i U \quad (3)$$

where X may an image to be analyzed, $W_i$ may be a probability matrix, and U may be a weighted image representation of a skin condition. $W_i$ may represent the respective probabilities that individual skin conditions U are in image to be analyzed X. For example, image to be analyzed X may be represented as weighted sum of weighted image representations of skin conditions U:

$$X=b_1 U_1+b_2 U_2 \ldots +b_i U_i \quad (4)$$

where b is a probabilistic weight (such as Q %). For example, $b_1 U_1$ may mean that condition $U_1$ (for example, eczema class 1) is determined to be present in image to be analyzed X with a probability of $b_1$%.

At block 228, in examples where the processor determines that the comparison value is below a threshold, the processor may be configured to receive an identification of the image to be analyzed as corresponding to a skin condition. For example, a physician may provide the identification as a particular one of the skin conditions whose weighted image representation is stored in memory. Processing may continue from block 228 to block 230.

At block 230, the processor may be configured to perform the component analysis to the image data of the image to be analyzed to generate a weighted component analysis result. The processor may also be configured to perform the sampling analysis. In some examples, the sampling analysis may be performed on the weighted component analysis result for the image data of the image to be analyzed. The sampling analysis may further be performed on the weighted component analysis results of the image data of the images of the particular one of the skin conditions. The sampling analysis may generate an updated weighted image representation for the particular one of the skin conditions. Processing may continue from block 230 to block 232.

At block 232, the processor may be configured to store the updated weighted image representation for the particular one of the skin conditions.

Among other benefits, a system in accordance with this disclosure can compare an image of a patient's skin with data in a memory including weighted image representations of identified skin conditions. The system may determine that the image of the patient's skin is a first percentage likely a first skin condition, a second percentage likely a second skin condition, etc. The image of the patient's skin can thus be determined to be like two or more skin conditions (e.g., 70% condition A, 20% condition B, 10% condition C, etc.).

FIG. 4 illustrates an example computer program product 300 for implementing analysis of representations of skin conditions arranged according to at least some embodiments presented herein. Program product 300 may include a signal bearing medium 302. Signal bearing medium 302 may include one or more instructions 304 that, when executed by, for example, a processor, may provide at least some of the functions described above with respect to FIGS. 1-3. Thus, for example, referring to system 100, processor 108 may undertake one or more of the blocks shown in FIG. 4 in response to instructions 304 conveyed to the system 100 by medium 302.

In some implementations, signal bearing medium 302 may encompass a computer-readable medium 306, such as, but not limited to, a hard disk drive, a Compact Disc (CD), a Digital Video Disk (DVD), a digital tape, memory, etc. In some implementations, signal bearing medium 302 may encompass a recordable medium 308, such as, but not limited to, memory, read/write (R/W) CDs, R/W DVDs, etc. In some implementations, signal bearing medium 302 may encompass a communications medium 310, such as, but not limited to, a digital and/or an analog communication medium (e.g., a fiber optic cable, a waveguide, a wired communications link, a wireless communication link, etc.). Thus, for example, program product 300 may be conveyed to one or more modules of the system 100 by an RF signal bearing medium 302, where the signal bearing medium 302 is conveyed by a wireless communications medium 310 (e.g., a wireless communications medium conforming with the IEEE 802.11 standard).

FIG. 5 is a block diagram illustrating some example computing devices 400 that are arranged for implementing analysis of representations of skin conditions arranged according to at least some embodiments presented herein. In a very basic configuration 402, computing device 400 typically includes one or more processors 404 and a system memory 406. A memory bus 408 may be used for communicating between processor 404 and system memory 406.

Depending on the desired configuration, processor 404 may be of any type including but not limited to a microprocessor (μP), a microcontroller (μC), a digital signal processor (DSP), or any combination thereof. Processor 404 may include one more levels of caching, such as a level one cache 410 and a level two cache 412, a processor core 414, and registers 416. An example processor core 414 may include an arithmetic logic unit (ALU), a floating point unit (FPU), a digital signal processing core (DSP Core), or any combination thereof. An example memory controller 418 may also be used with processor 404, or in some implementations memory controller 418 may be an internal part of processor 404.

Depending on the desired configuration, system memory 406 may be of any type including but not limited to volatile memory (such as RAM), non-volatile memory (such as ROM, flash memory, etc.) or any combination thereof. System memory 406 may include an operating system 420, one or more applications 422, and program data 424. Application 422 may include a generation and analysis of representations of skin conditions algorithm 426 that may be arranged to perform one or more of the functions as described herein including those described with respect to FIGS. 1-4. Program data 424 may include image data 428 that may be useful for generation and analysis of representations of skin conditions as is described herein. In some embodiments, application 422 may be arranged to operate with program data 424 on operating system 420 such that generation and analysis of representations of skin conditions may be provided. This described basic configuration 402 is illustrated in FIG. 5 by those components within the inner dashed line.

Computing device 400 may have additional features or functionality, and additional interfaces to facilitate communications between basic configuration 402 and any required devices and interfaces. For example, a bus/interface controller 430 may be used to facilitate communications between basic configuration 402 and one or more data storage devices 432 via a storage interface bus 434. Data storage devices 432 may be removable storage devices 436, non-removable storage devices 438, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 406, removable storage devices 436 and non-removable storage devices 438 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 400. Any such computer storage media may be part of computing device 400.

Computing device 400 may also include an interface bus 440 for facilitating communication from various interface devices (e.g., output devices 442, peripheral interfaces 444, and communication devices 446) to basic configuration 402 via bus/interface controller 430. Example output devices 442 include a graphics processing unit 448 and an audio processing unit 450, which may be configured to communicate to various external devices such as a display or speakers via one or more A/V ports 452. Example peripheral interfaces 444 include a serial interface controller 454 or a parallel interface controller 456, which may be configured to communicate with external devices such as input devices (e.g., keyboard, mouse, pen, voice input device, touch input device, etc.) or other peripheral devices (e.g., printer, scanner, etc.) via one or more I/O ports 458. An example communication device 446 includes a network controller 460, which may be arranged to facilitate communications with one or more other computing devices 462 over a network communication link via one or more communication ports 464.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 400 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 400 may also be implemented as a personal computer including both laptop computer and non-laptop computer configurations.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for generating a representation of a skin condition, the method comprising:

storing, in a memory, image data, the image data including first image data relating to a first image of a skin condition and second image data relating to a second image of the skin condition, the second image being different from the first image;

receiving, at a processor, the image data;

performing, by the processor, a component analysis of the first image data to generate a first weighted component analysis result for the first image data, wherein the first weighted component analysis result represents the first image data as a weighted sum of components, wherein the components are based on one of skin color, skin contrast, skin tone, and gamma correction related to the skin;

performing, by the processor, the component analysis of the second image data to generate a second weighted component analysis result for the second image data, wherein the second weighted component analysis result represents the second image data as a weighted sum of the components, wherein the components are based on one of skin color, skin contrast, skin tone, and gamma correction related to the skin; and performing, by the processor, a sampling analysis to the first weighted component analysis result and the second weighted component analysis result to generate a weighted image representation for the skin condition, wherein the weighted image representation represents the skin condition as a weighted sum of the components.

2. The method of claim 1, wherein: the component analysis is an independent component analysis; and
the sampling analysis is a nested sampling analysis.

3. The method of claim 1, wherein the components are based on at least one of color, contrast, skin tone, or gamma correction.

4. The method of claim 1, further comprising: receiving, at the processor, third image data including a third image relating to a second skin condition;

determining, by the processor, a value of at least one image component of the third image; and comparing, by the processor, the value of the at least one image component of the third image data with a corresponding image component of the weighted image representation for the skin condition.

5. The method of claim 4, further comprising:

generating, by the processor, a comparison value based on the comparing, the comparison value representing a likelihood that the second skin condition is the first skin condition.

6. The method of claim 5, further comprising:
comparing, by the processor, the comparison value to a threshold value; and displaying, on a display, the comparison value when the comparison value is greater than the threshold.

7. A system effective to generate a representation of a skin condition, the system comprising:
a memory configured to store image data, the image data including first image data relating to a first image of a skin condition and second image data relating to a second image of the skin condition, the second image being different from the first image; and
a processor in communication with the memory, wherein the processor is effective to receive the image data,
perform a component analysis of the first image data to generate a first weighted component analysis result for the first image data, wherein the first weighted component analysis result represents the first image data as a weighted sum of components, wherein the components are based on one of skin color, skin contrast, skin tone, and gamma correction related to the skin,
perform the component analysis of the second image data to generate a second weighted component analysis result for the second image data, wherein the second weighted component analysis result represents the second image data as a weighted sum of the components, wherein the components are based on one of skin color, skin contrast, skin tone, and gamma correction related to the skin;
perform a sampling analysis to the first weighted component analysis result and the second weighted component analysis result to generate a weighted image representation for the skin condition, wherein the weighted image representation represents the skin condition as a weighted sum of the components; and store the weighted image representation in the memory.

8. The system of claim 7, further comprising: a scanner, in communication with the processor, the scanner effective to generate the image data.

9. The system of claim 7, wherein: the component analysis is an independent component analysis; and the sampling analysis is a nested sampling analysis.

10. The system of claim 7, wherein the components are based on at least one of color, contrast, skin tone, or gamma correction.

11. The system of claim 7, wherein the processor is further effective to receive third image data including a third image relating to a second skin condition, determine a value of at least one image component of the third image; and
compare the value of the at least one image component of the third image data with a corresponding image component of the weighted image representation for the skin condition.

12. The system of claim 11, wherein the processor is further effective to generate a comparison value, wherein the comparison value represents a likelihood that the second skin condition is the first skin condition.

13. The system of claim 12, wherein the processor is further effective to compare the comparison value to a threshold value.

14. The system of claim 13, further comprising a display in communication with the processor, wherein the display is effective to display the comparison value when the comparison value is greater than the threshold.

15. A method of analyzing image representations of skin conditions, the method comprising:
storing, in a memory, image data of a plurality of images of a plurality of skin conditions;
receiving, at a processor, at least some of the image data of the plurality of images of the plurality of skin conditions;
performing, by the processor, a component analysis of the at least some of the image data of the plurality of images of the plurality of skin conditions to generate a weighted component analysis result for the at least some of the image data,
wherein the components are based on one of skin color, skin contrast, skin tone, and gamma correction related to the skin;
performing, by the processor, a sampling analysis to a plurality of weighted component analysis results of at least some of the plurality of skin conditions to generate a weighted image representation for the at least some of the plurality of skin conditions; and
storing, in the memory, the weighted image representation for the at least some of the plurality of skin conditions; wherein each weighted image representation comprises a plurality of weighted image components.

16. The method of claim 15, wherein: the component analysis is an independent component analysis; and the sampling analysis is a nested sampling analysis.

17. The method of claim 15, wherein the image components are based on at least one of color, contrast, skin tone, or gamma correction.

18. The method of claim 15, further comprising:
receiving at the processor image data of an image to be analyzed;
determining, by the processor, a value of at least some of the image components of the image data of the image to be analyzed;
comparing, by the processor, the value of the at least some of the image components of the image data of the image to be analyzed with a corresponding image component of a weighted image representation for a skin condition;
generating, by the processor, a comparison value based on the comparison, the comparison value representing a likelihood that the image to be analyzed corresponds to the skin condition; and
repeating, by the processor, the comparing and generating for at least some of the weighted image representations of at least some of the plurality of skin conditions.

19. The method of claim 18, further comprising: comparing the comparison value to a threshold value; and
displaying, on a display, the comparison value when the comparison value is greater than the threshold.

20. The method of claim 18, further comprising: storing, in the memory, the weighted component analysis result for at least some of the image data; storing, in the memory, the image data of the image of the skin condition to be analyzed;
when at least some of the comparison values are below a threshold, receiving an identification of the image to be analyzed as a particular one of the skin conditions;
applying, by the processor, the component analysis to the image data of the image to be analyzed to generate a weighted component analysis result for the image data of the image to be analyzed;
applying, by the processor, the sampling analysis to the weighted component analysis result for the image data of the image to be analyzed and the weighted component analysis results of the image data of the images of the particular one of the skin conditions to generate an updated weighted image representation for the particular one of the skin conditions; and storing, in the memory, the updated weighted image representation.

\* \* \* \* \*

UNITED STATES PATENT AND TRADEMARK OFFICE
CERTIFICATE OF CORRECTION

PATENT NO. : 8,478,009 B2  
APPLICATION NO. : 12/971140  
DATED : July 2, 2013  
INVENTOR(S) : Leong Chung Wei Page 1 of 1

It is certified that error appears in the above-identified patent and that said Letters Patent is hereby corrected as shown below:

Title Page 2, in Item (56), under "OTHER PUBLICATIONS", in Column 1, Line 12, delete "Tabatabaie, k.; Esteki, A.;," and insert -- Tabatabaie, k., Esteki, A., --, therefor.

In the Drawings

In Fig. 5, Sheet 5 of 15, below "PROCESSOR (404)" delete "uP/uC / DSP" and insert -- µP/µC/DSP --, therefor.

Signed and Sealed this  
Twenty-ninth Day of October, 2013

Teresa Stanek Rea  
*Deputy Director of the United States Patent and Trademark Office*